(12) United States Patent
Hart et al.

(10) Patent No.: US 9,662,102 B2
(45) Date of Patent: May 30, 2017

(54) SUTURE HOLDING SYSTEM

(75) Inventors: Rickey Hart, Marco Island, FL (US); Thore Zantop, Muenster (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 727 days.

(21) Appl. No.: 12/367,247

(22) Filed: Feb. 6, 2009

(65) Prior Publication Data

US 2010/0204731 A1 Aug. 12, 2010

(51) Int. Cl.
*A61B 17/04* (2006.01)

(52) U.S. Cl.
CPC .. *A61B 17/0401* (2013.01); *A61B 2017/0409* (2013.01); *A61B 2017/0417* (2013.01); *A61B 2017/0459* (2013.01); *A61B 2017/0464* (2013.01)

(58) Field of Classification Search
CPC ........ A61B 17/0401; A61B 2017/0414; A61B 2017/0417; A61B 2017/0459; A61B 2017/0464; A61B 2017/0409; A61B 2017/0419; A61B 2017/0448; A61B 2017/0456; A61B 2017/0475; A44B 1/00; A44B 1/185; A44B 1/18; Y10T 24/3916; Y10T 24/3918
USPC ................ 606/72, 73, 232; 623/13.13, 13.14
See application file for complete search history.

(56) References Cited

U.S. PATENT DOCUMENTS

| 74,070 A | * | 2/1868 | Fletcher | F16G 11/00 24/129 B |
| 757,820 A | * | 4/1904 | Lykke | F16G 11/10 24/130 |
| 1,806,162 A | * | 5/1931 | Hahn | A43C 7/04 24/129 B |

(Continued)

FOREIGN PATENT DOCUMENTS

| JP | 2004515273 A | 5/2004 |
| WO | 0139671 A1 | 6/2001 |

(Continued)

OTHER PUBLICATIONS

Smith & Nephew Technique Plus™ Illustrated Guide, Meniscal Repair with the FasT-Fix™ Suture System, Smith & Nephew, Inc., Andover, MA 01810 USA, Mar. 2002, 1061031 Rev. B (11 pages).

(Continued)

*Primary Examiner* — Eric Rosen
*Assistant Examiner* — Lucas Paez
(74) *Attorney, Agent, or Firm* — Whitmyer IP Group LLC

(57) ABSTRACT

A suture holding system including a suture and a block having first, second and third regions for receiving the suture, having proximal and distal ends, is provided. The suture is received in the first and second regions of the block, defining a first suture portion, and is then received in the third region before passing between the block and the first suture portion, defining a second suture portion. In this configuration, pulling on the distal end of the suture selectively locks the suture to block, whereas pulling on the proximal end of the suture allows the suture to advance (Continued)

freely in that direction. Suture holding system may also include a second block, being rotated 180 degrees with respect to the first block. A delivery device for implanting the suture holding system in soft tissue and methods for repairing a tear in soft tissue are also provided.

20 Claims, 13 Drawing Sheets

(56) References Cited

U.S. PATENT DOCUMENTS

| | | | | |
|---|---|---|---|---|
| 3,880,166 | A * | 4/1975 | Fogarty | 606/158 |
| 4,823,794 | A * | 4/1989 | Pierce | 606/232 |
| 5,210,911 | A * | 5/1993 | Brown | B65D 63/16 24/129 B |
| 5,693,060 | A * | 12/1997 | Martin | 606/148 |
| 6,317,935 | B1 * | 11/2001 | O'Rouke | A62B 1/04 24/115 K |
| 6,635,073 | B2 * | 10/2003 | Bonutti | 606/232 |
| 6,652,561 | B1 * | 11/2003 | Tran | 606/232 |
| 6,972,027 | B2 * | 12/2005 | Fallin et al. | 606/232 |
| 7,153,312 | B1 | 12/2006 | Torrie et al. | |
| 7,594,923 | B2 * | 9/2009 | Fallin et al. | 606/232 |
| 7,722,644 | B2 * | 5/2010 | Fallin et al. | 606/232 |
| 7,887,551 | B2 * | 2/2011 | Bojarski et al. | 606/139 |
| 2002/0019649 | A1 | 2/2002 | Sikora et al. | |
| 2003/0130694 | A1 | 7/2003 | Bojarski et al. | |
| 2004/0002734 | A1 | 1/2004 | Fallin et al. | |
| 2005/0251157 | A1 | 11/2005 | Saadat et al. | |
| 2005/0288709 | A1 | 12/2005 | Fallin et al. | |
| 2005/0288711 | A1 | 12/2005 | Fallin et al. | |
| 2008/0140092 | A1 | 6/2008 | Stone et al. | |
| 2011/0270278 | A1 | 11/2011 | Overes et al. | |
| 2012/0172924 | A1 | 7/2012 | Allen, IV | |
| 2012/0184972 | A1 | 7/2012 | Lam et al. | |

FOREIGN PATENT DOCUMENTS

| | | |
|---|---|---|
| WO | 0236020 A1 | 5/2002 |
| WO | 2012096706 A1 | 7/2012 |
| WO | 2012151592 A2 | 11/2012 |

OTHER PUBLICATIONS

Arthrex product advertisement; "Meniscal Clinch (TM)"; www.arthrex.com; ARTHREX, Inc.; 2009 (retrieved from internet Sep. 10, 2009; web site developed Nov. 1998); 1 page.
Canadian Office Action; Application No. CA 2,692,206; Issued: Oct. 19, 2011; 3 pages.
European Search Report; Application No. EP 10 15 2824; Issued: Jun. 8, 2010; 6 pages.
European Search Report Application No. EP 13 19 5808 Completed: Feb. 28, 2014; Mailing Date: Mar. 11, 2014 5 pages.
Partial European Search Report Application No. EP 13 19 5554 Completed: Feb. 28, 2014; Mailing Date: Mar. 11, 2014 7 pages.
European Search Report Application No. EP 13 19 5554 Completed: Jul. 14, 2014; Mailing Date: Jul. 23, 2014 13 pages.

* cited by examiner

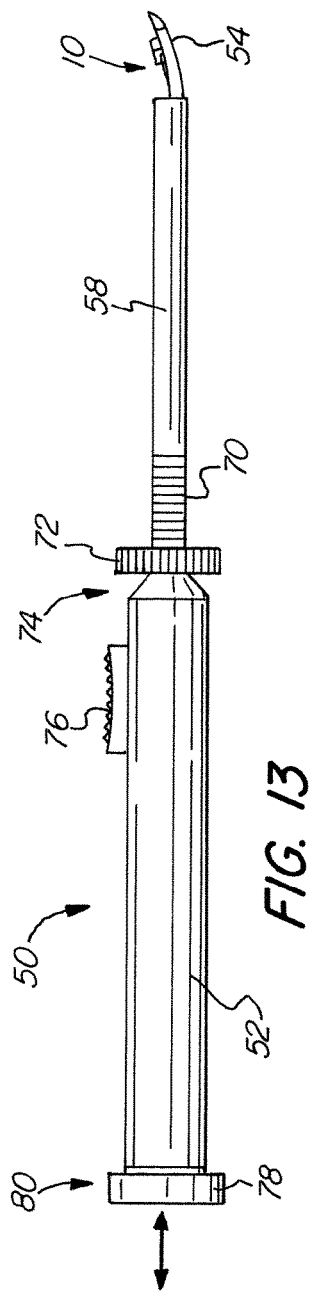
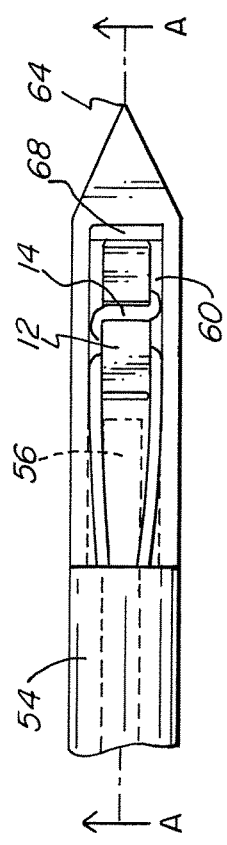
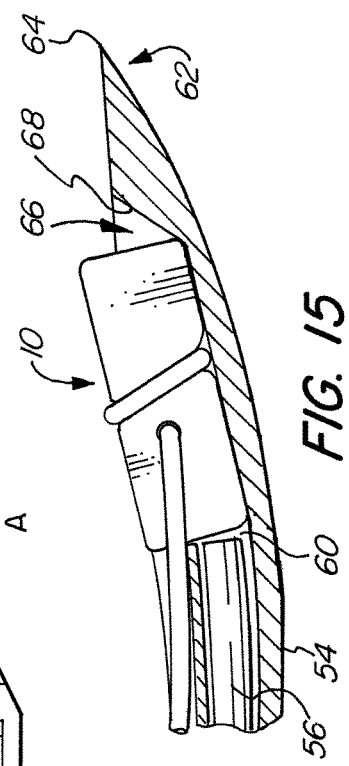
FIG. 13
FIG. 14
FIG. 15

SUTURE HOLDING SYSTEM

FIELD OF THE INVENTION

The present invention relates to suture holders, specifically, suture holders used in soft tissue repair as well as delivery devices and methods for using such holders.

BACKGROUND OF THE INVENTION

When a soft tissue, or a portion of a tissue, such as muscle, ligament, or cartilage, tears, surgery to repair the detached soft tissue is often required. The goal of such surgery is to suture the torn portion of the tissue to thereby repair the tear and reconstitute the tissue back to its original status. Traditionally, repair was accomplished by sewing the tissue together with two needles and a suture, then tying knots to secure the suture within the tissue. To simplify the wound closure procedure and to improve fixation, various types of suture anchors have been developed, such as those described in U.S. Pat. No. 7,153,312 B1 to Torrie et al. and U.S. Pat. No. 6,972,027 B2 to Fallin et al.

Torrie et al. disclose a closure device for repairing a tear in soft tissue comprising a suture coupled with two fixation members. Each fixation member comprises two holes through which the suture is received. The suture is immovably fixed to the first fixation member, but is freely movable relative to the second fixation member. Therefore, a retaining element, in the form of a slip knot or overhand knot, must be provided on the free end of the suture to prevent the suture from loosening between the fixation members when a tension is applied. When an overhand knot is used, the surgeon must use a knot pusher in order to shorten the length of suture between the fixation members and close the tear. As illustrated in FIGS. 2A-2I and 13-13B, the knots required by this system are particularly complicated to tie and correctly position.

Fallin et al. disclose a suture anchor delivery system comprising two suture anchors secured together by a suture. Similar to Torrie et al., the suture is immovably fixed to the first fixation member. The suture is received in the second fixation member such that pulling on the loose end of the suture causes it to selectively lock to the second anchor. Once the fixation members are implanted, tightening the portion of the suture between them requires a highly coordinated procedure. The surgeon must simultaneously pull back on both free ends of a retraction line and the free end of the suture to cause the suture to unlock from the second fixation device. Then, while continuing to pull back on the free end of the suture, the surgeon must slowly release the retraction line at a complementary rate. If necessary, this process is repeated until all of the slack is removed from between the anchors.

Unfortunately, the devices of Torrie et al. and Fallin et al. are unsatisfactory for a variety of reasons. What is desired, therefore, is a suture holding system for use in the repair of soft tissue tears that does not require the use of knots, knot pushers, and retraction lines in order to implant and utilize the devices.

SUMMARY OF THE INVENTION

Accordingly, it is an object of the present invention to provide a suture holder that can selectively lock a suture to the holder without the use of knots or the like.

It is a further object of the present invention to provide a suture holder that can selectively tighten a portion of suture placed across a tear in tissue without the use of retraction lines or the like.

It is yet a further object of the present invention to provide a suture holder that is quickly and easily attached to a suture.

These and other objects and advantages are achieved by providing a suture holding system comprising a block and a suture having a first portion and a second portion. The block has a hole extending therethrough, and a first notch extending along at least a portion of the block. A first suture portion is received in the hole and the first notch and a second suture portion is held against the block by said first suture portion. In some embodiments, the block further comprises a second notch extending along at least a portion of the block and the second suture portion is then at least partially received in the second notch before passing between the first suture portion and the block. The suture holding system may also comprise a second block.

The block is substantially rectangular in shape in some embodiments and may have a tapered edge in others. The block has a length, height, and depth. The block length may be about 2.5 times longer than its height or may be about 3 times longer than its height. The block height may be about 1.5 times longer than its depth or may be about 2 times longer than its depth.

In a further embodiment, the suture holding system comprises a suture having a first portion and a second portion and a block having a first hole extending therethrough, a front surface, a bottom surface, and a top surface. The first suture portion is received in the first hole and passes under the block bottom surface. The second suture portion passes from the bottom surface over the top surface before being held against the block front surface by the first suture portion.

The block may further comprise a notch extending along at least a portion of the top surface of the block, the second suture portion being received in the notch before passing between the first suture portion and the front surface of the block. In another embodiment, the block may further comprise a first notch extending along at least a portion of the bottom surface of the block, the first suture portion being received in the first hole and said the notch. In a further embodiment, the block further comprises a second notch extending along at least a portion of the top surface of the block, the second suture portion being received in the second notch before passing between the first suture portion and the front surface of the block. In yet another embodiment, the block further comprises a second hole extending therethrough, the first suture portion being received in the first hole and the second hole. The block may, in another embodiment, further comprise a notch extending along at least a portion of the top surface of the block, the second suture portion being received in the notch before passing between the first suture portion and the front surface of the block.

A suture holding system comprising a suture having a first portion and a second portion and a first block comprising a first region for receiving a portion of a suture, a second region for receiving a portion of a suture and a third region for receiving a portion of a suture is also provided. The first suture portion is received in the first region and the second region, the second suture portion being at least partially received in the third region before being held against the first block by the first suture portion.

The first region may comprise a hole extending through at least a portion of the first block. The second region may comprise a hole extending through at least a portion of the first block or a notch extending along at least a portion of the first block. The third region may comprise a notch extending along at least a portion of the first block.

A second block for receiving a portion of the suture is also provided. In some embodiments, the second block is rotated 180 degrees with respect to the first block. The second block comprises a fourth region for receiving a portion of a suture, a fifth region for receiving a portion of a suture, and a sixth region for receiving a portion of a suture. The suture further comprises a third portion and a fourth portion, the third suture portion being at least partially received in the fourth region and the fifth region, the fourth suture portion being at least partially received in the sixth region before being held against the second block by the third suture portion.

The fourth region may comprise a hole extending through at least a portion of the second block. The fifth region may comprise a hole extending through at least a portion of the second block or a notch extending along at least a portion of the second block. The sixth region may comprise a notch extending along at least a portion of the second block.

A suture holding system comprising a block having a first hole extending therethrough and a second hole extending therethrough and a suture having a first portion and a second portion is also provided. In this embodiment, the first suture portion is received in the first hole and the second hole, and the second suture portion is held against the block by the first suture portion. In some embodiments, the block may also comprise a notch extending along at least a portion of the block, said second suture portion being received in said notch before passing between said first suture portion and said block.

A suture holder delivery system comprising a housing, a delivery needle at least partially slidably received within the housing, and a driver rod at least partially slidably received within the housing is also provided. In other embodiments, the suture holder delivery system further comprises an actuator in communication with the driver rod. The needle may be curved at the proximal end.

The delivery system further comprises a suture having a first portion and a second portion, and a first block having a hole extending therethrough and a first notch extending along at least a portion of the block. The first suture portion is at least partially received in the hole and the first notch and the second suture portion is held against the block by the first suture portion. In some embodiments, the suture holder delivery system further comprises a second notch extending along at least a portion of the block, the second suture portion being at least partially received in the second notch before passing between the first suture portion and the block.

In some embodiments, the delivery needle has a proximal end and a distal end. In a further embodiment, the driver rod is distal of said first block. In yet another embodiment, the suture holder delivery system comprises a second block, which may be arranged distal of the first block.

In another embodiment, the first block further comprises a longitudinal hole extending therethrough and the needle may be at least partially slidably received within the longitudinal hole. The driver rod may further comprise a tube that is at least partially slidably received over the needle.

In yet another embodiment, the needle comprises an interior passage and the first block and the driver rod may be at least partially slidably received within the needle interior passage.

A method for repairing a tear in soft tissue comprising the steps of placing a first block in a portion of soft tissue, providing a suture having a first portion, a second portion, a proximal end and a connecting portion distal of the first block and passing at least partially through the tear, and pulling on the suture proximal end to shorten the connecting portion of the suture is also provided. The first block has a first region for receiving a portion of a suture, a second region for receiving a portion of a suture, and a third region for receiving a portion of a suture. The first suture portion is at least partially received in the first region and second region, the second suture portion being at least partially received in the third region before passing between the first block and the first suture portion.

The method may further comprise the step of placing a second block into the soft tissue, the suture passing through at least a portion of the second block. The second block may be distal of said first block. The suture connecting portion may be provided between the first block and the second block. The second block may comprise a fourth region for receiving a portion of a suture, a fifth region for receiving a portion of a suture, and a sixth region for receiving a portion of a suture. In a further embodiment, the method further comprises the step of providing a suture having a third portion and a fourth portion, the suture third portion being at least partially received in the fourth region and the fifth region, the suture fourth portion being at least partially received in the sixth region before passing between the second block and the suture third portion.

BRIEF DESCRIPTION OF THE DRAWINGS

FIG. 13 is a side view of an embodiment of the delivery device for use with the suture holding system of the present invention.

FIG. 14 is a partial top view of an embodiment of the delivery device for use with the suture holding system of the present invention.

FIG. 15 is a partial side sectional view, taken along line A, of an embodiment of the delivery device for use with the suture holding system of the present invention.

DETAILED DESCRIPTION OF THE INVENTION

Figure 1:
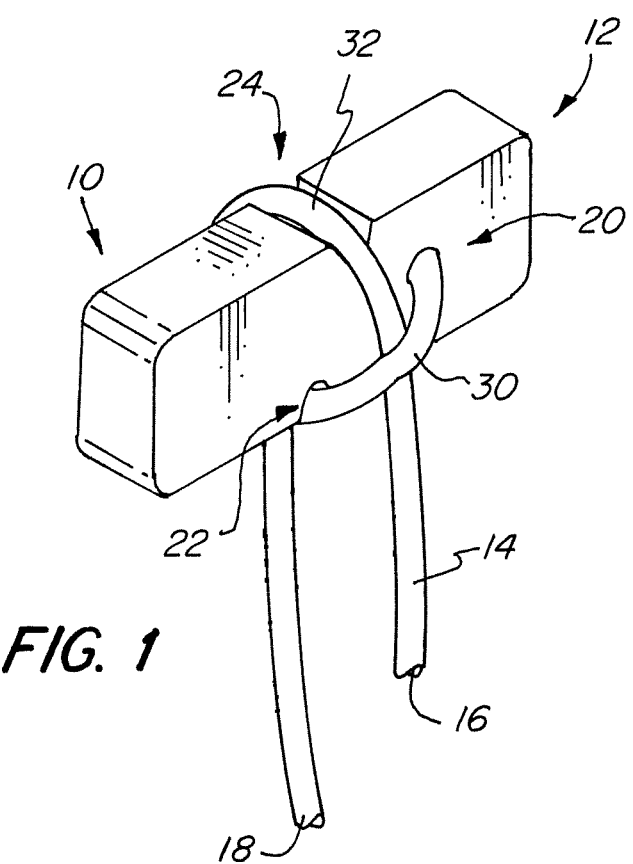
FIG. 1 is a perspective view of an embodiment of the suture holding system of the present invention.
Figure 2:
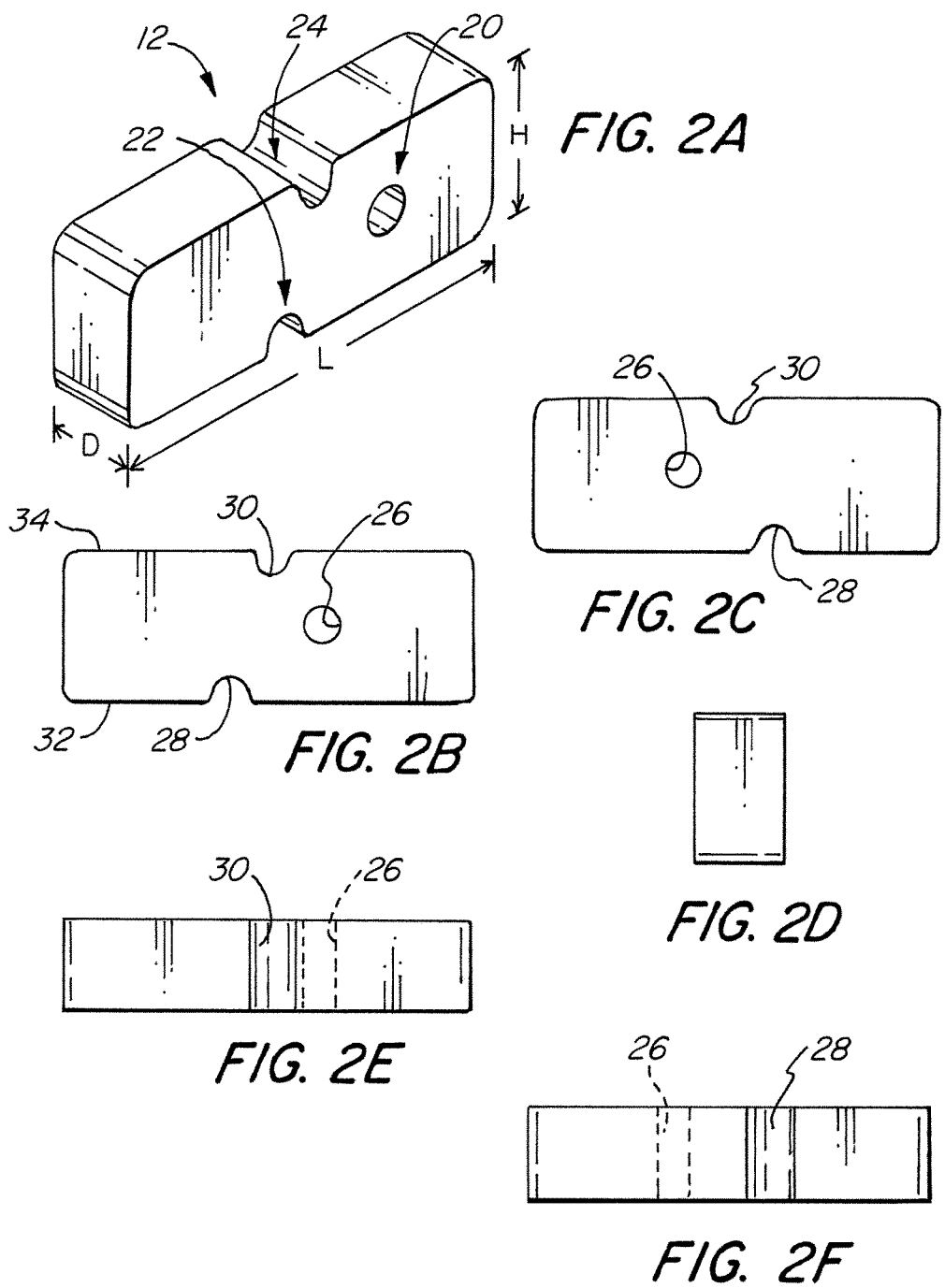
FIG. 2A is a perspective view of an embodiment of the block as used in the suture holding system of the present invention.
FIG. 2B is a front view of an embodiment of the block as used in the suture holding system of the present invention.
FIG. 2C is a back view of an embodiment of the block as used in the suture holding system of the present invention.
FIG. 2D is a side view of an embodiment of the block as used in the suture holding system of the present invention.
FIG. 2E is a top view of an embodiment of the block as used in the suture holding system of the present invention.
FIG. 2F is a bottom view of an embodiment of the block as used in the suture holding system of the present invention.

The novel suture holding system 10 of the present invention, comprising a block 12 and a suture 14 having proximal 16 and distal 18 ends, is depicted in FIG. 1. Block 12 defines first 20, second 22, and third 24 regions for receiving a portion of suture 14. In one embodiment, first region 20 is provided as a hole 26 extending through the block 12, second region 22 is provided as a lateral notch 28 on the bottom surface 32 of the block 12, and third region 24 is provided as a lateral notch 30 on the top surface 34 of the block 12. As used in the specification and appended claims, the term "suture" is intended to include any type of flexible line, but typically comprises medical grade suture.

As shown in FIGS. 2A-2F, block 12 is generally rectangular in cross section and profile, having a length L, height H and depth D. In alternative embodiments, it is appreciated that the edges of block 12 may be rounded or chamfered. The block length can range from about 2.5 to about 3 times longer than the block height. The block height can range from about 1.5 to about 2 times longer than the block depth. In a preferred embodiment, the block is 7 mm long, 2.4 mm high, and 1.5 mm deep. In another preferred embodiment, shown in FIGS. 18A-18F, the block is 5 mm long, 2 mm high, and 1.2 mm deep. Other block shapes and dimensions are possible and are contemplated herein as alternative embodiments.

Figure 3:
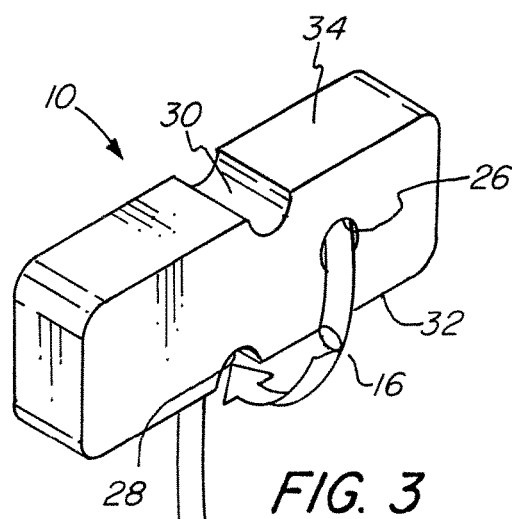
FIG. 3 is a perspective view of an embodiment of the suture holding system of the present invention, demonstrating how the suture is attached to the block.
Figure 4:
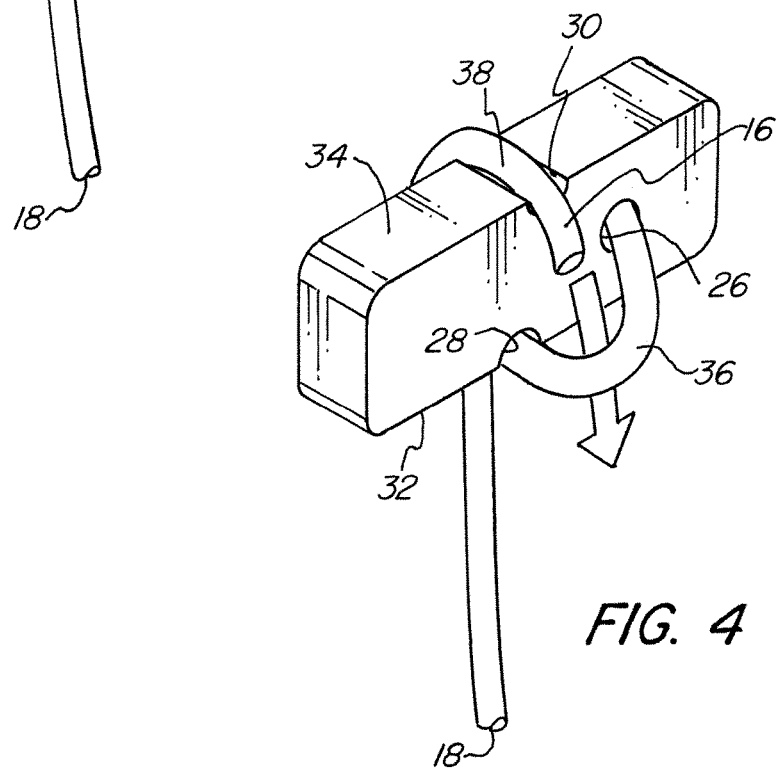
FIG. 4 is a perspective view of an embodiment of the suture holding system of the present invention, demonstrating how the suture is attached to the block.

Referring now to FIGS. 3 and 4, suture 14 is attached to block 12 by threading proximal end 16 of suture 14 through hole 26 and then through notch 28, defining a first suture portion 36. Proximal end 16 is then wrapped around the block 12 and received in notch 30 before passing between first suture portion 36 and the block 12, defining a second suture portion 38. In this configuration, pulling on distal end 18 of suture 14 selectively locks suture 14 to block 12 without the need for any type of knot or retaining element. When distal end 18 of suture 14 is pulled taught, first suture portion 36 tightens, pressing second suture portion 38 against the block 12 and preventing the suture 14 from advancing further in the distal direction. However, pulling proximal end 16 of suture 14 allows the suture 14 to advance freely in the proximal direction.

Figure 5:
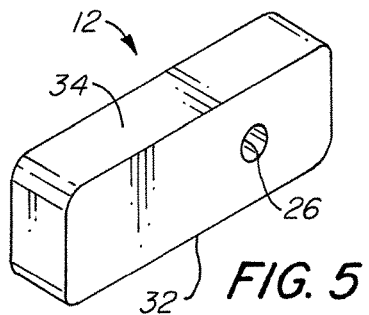
FIG. 5 is a perspective view of an embodiment of the block as used in the suture holding system of the present invention.
Figure 10:
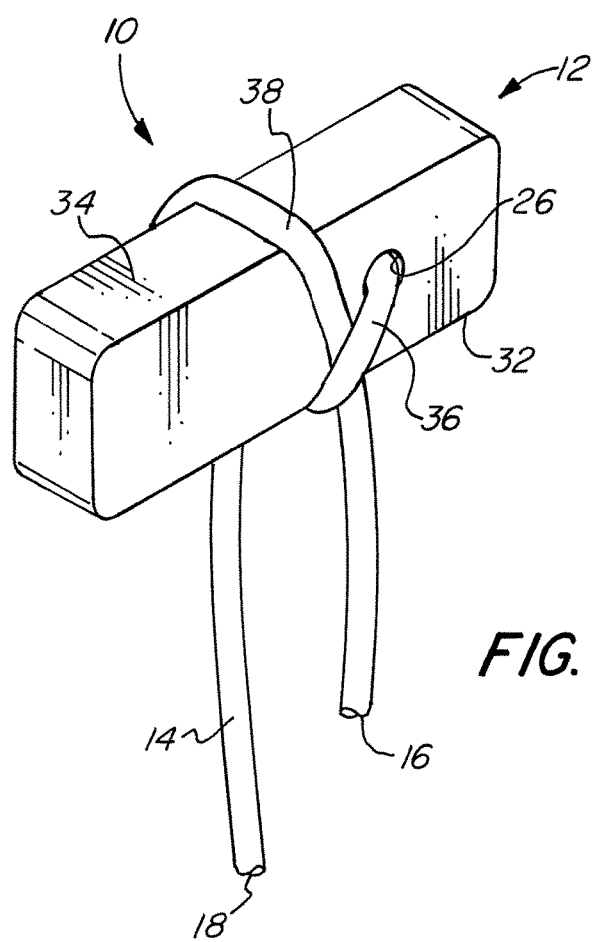
FIG. 10 is a perspective view of an embodiment of the suture holding system of the present invention.

Many other operative configurations of the first 20, second 22, and third 24 regions of block 12, in addition to the combination shown in FIG. 1, are contemplated herein. For example, in the embodiment of FIG. 5, first region 20 is provided as a hole 26, second region 22 is the bottom surface 32 of the block 14, and third region 24 is the top surface 34 of the block 14. In this configuration, as shown in FIG. 10, suture 14 is attached to block 12 by threading the proximal end 16 of suture 14 through hole 26 and then under the bottom surface 32 of block 12, defining first suture portion 36. Proximal end 16 is then wrapped around the block 12 and over the top surface 34 before passing between first suture portion 36 and the block 12, defining a second suture portion 38. Again, when distal end 18 of suture 14 is pulled taught first suture portion 36 tightens, pressing second suture portion 38 against the block 12 and preventing the suture 14 from advancing in the distal direction.

Figure 6:
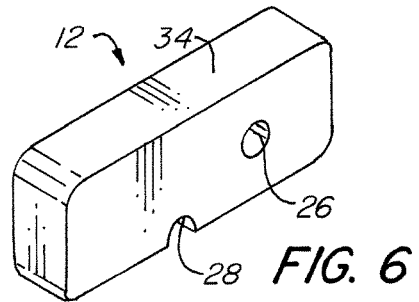
FIG. 6 is a perspective view of an embodiment of the block as used in the suture holding system of the present invention.
Figure 7:
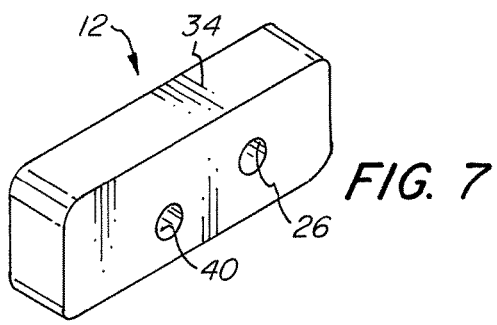
FIG. 7 is a perspective view of an embodiment of the block as used in the suture holding system of the present invention.
Figure 8:
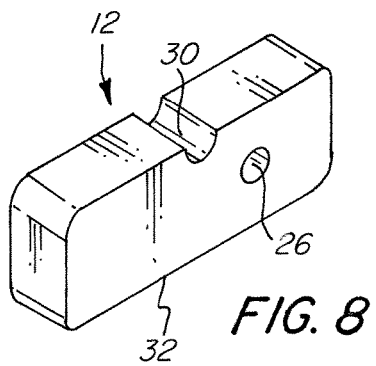
FIG. 8 is a perspective view of an embodiment of the block as used in the suture holding system of the present invention.
Figure 9:
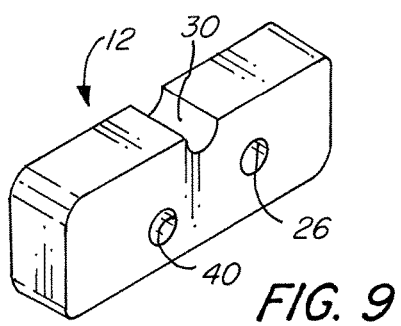
FIG. 9 is a perspective view of an embodiment of the block as used in the suture holding system of the present invention.

Other configurations include hole 26, lateral notch 28 and the top surface 34 of the block 12 (FIG. 6); hole 26, hole 40, and the top surface 34 of the block 12 (FIG. 7); hole 26, the bottom surface 32 of the block 12, and lateral notch 30 (FIG. 8); and hole 26, hole 40, and lateral notch 30 (FIG. 9). The particular position of the holes and notches on the block 12 shown in these figures is merely exemplary and other positions are possible without loss of functionality of the block 12. It is also appreciated that first 20, second 22, and third 24 regions may be inverted without any loss in functionality such that third region 24 is oriented near bottom surface 32.

Figure 11:
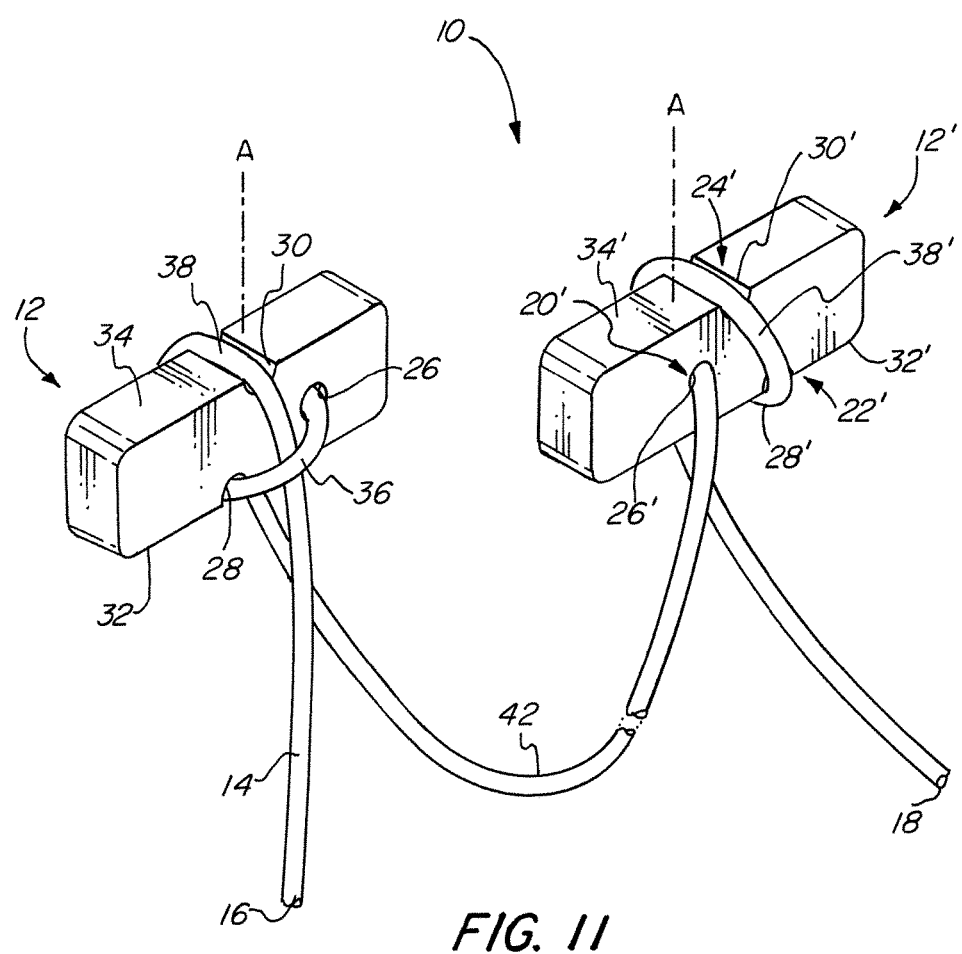
FIG. 11 is a perspective view of an embodiment of the suture holding system of the present invention having two blocks.

The suture holding system 10 of the present invention may also comprise a second block 12'. Referring now to FIG. 11, second block 12' is rotated 180 degrees with respect to first block 12 around an axis A and defines first 20', second 22', and third 24' regions for receiving a portion of suture 14. In one embodiment, first region 20' is provided as a hole 26' extending through block 12', second region 22' is provided as a lateral notch 28' on the bottom surface 32' of block 12', and third region 24' is provided as a lateral notch 30' on the top surface 34' of block 12'. Second block 12' may have any of the above-described alternative configurations as block 12.

Suture 14 is attached to block 12 as described above. As shown in FIG. 11, suture 14 is then attached to block 12' by threading distal end 18 through hole 26' and then through notch 28', defining a first suture portion 36' (not shown).

Figure 12:
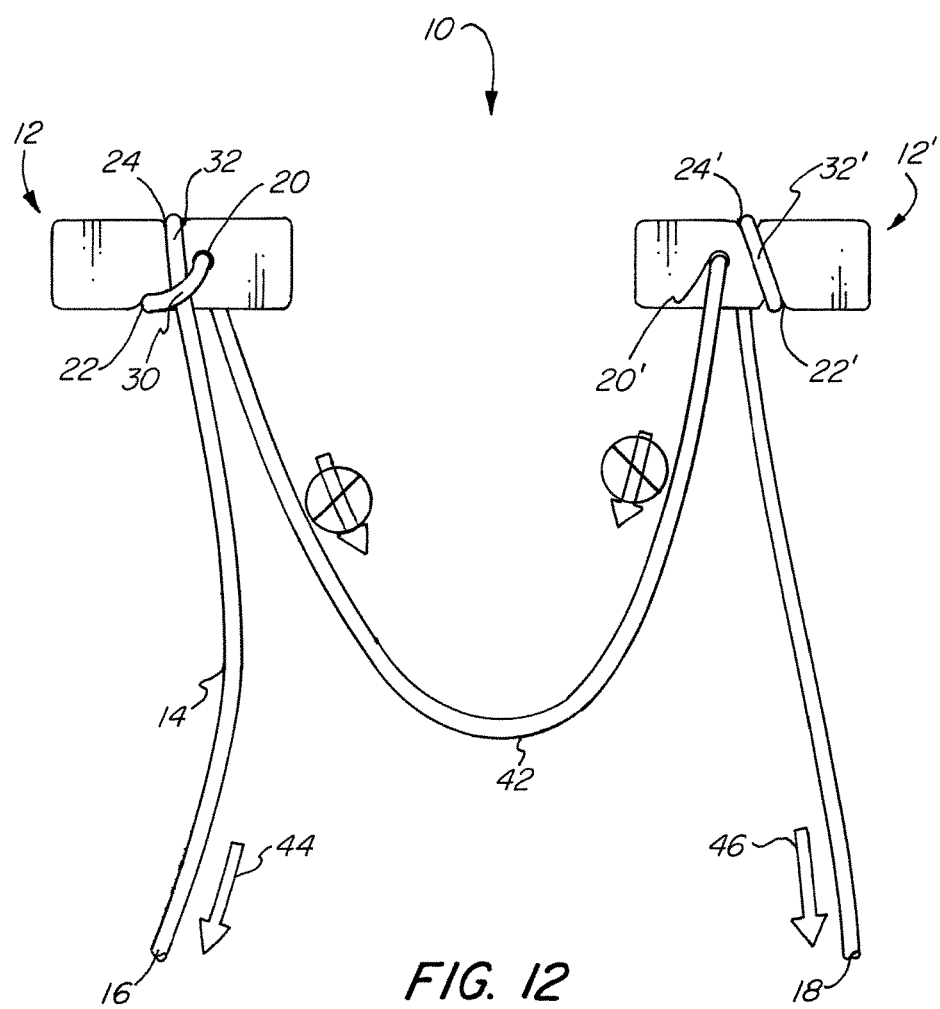
FIG. 12 is a front view of an embodiment of the suture holding system of the present invention, illustrating the selective locking of the suture with respect to each block.

Distal end 18 is then wrapped around the block 12' and received in notch 30' before passing between first suture portion 36' and the block 12', defining a second suture portion 38'. A connecting portion 42 of the suture 14 is defined between block 12 and block 12'. The configuration of first 22, 22', second 24, 24' and third 26, 26' regions, and the rotation of second block 12' with respect to first block 12", allows suture 14 to be pulled in the direction of arrows 44 and 46, but does not allow tension placed on connecting portion 42 to pull suture 14 in the opposite direction through the blocks 12, 12'. This is illustrated in FIG. 12.

A delivery device 50 configured for implanting the blocks 12, 12' of the suture holding system 10 into soft tissue so as to facilitate repair of a tear in soft tissue is shown in FIGS. 13-15. Delivery device 50 comprises a needle 54 and a driver rod 56, both at least partially slidably received within a housing 58, and a handle 52. Handle 52 may have a variety of cross sectional shapes, such as, but not limited to, circular, square, rectangular, oblong, triangular, and the like. Needle 54 has a hollow interior passage 60 and both the driver rod 56 and suture holding system 10 are slidably received therein. Proximal end 62 of the needle 54 may be closed, and preferably, may terminate in a pointed tip 64 to aid in penetration of the tissue. In the embodiment shown in FIG. 15, needle 54 is curved upward at its proximal end 62. It will be appreciated that depending on the intended use of the suture holding system 10, the proximal end 62 of needle 54 may be straight along its length, or may be curved or bent into a variety of alternative configurations.

Needle 54 is typically made of a metal, such a stainless steel, but can also be made of plastic, composite, or other desired material. Where needle 54 is straight, driver rod 56 can be made of the same material as needle 54. Where needle 54 is curved, however, driver rod 56 is typically made of a material stiff enough to advance a block 12 of suture holding system 10 through interior passage 60, but flexible enough to conform to the contour of needle 54. For example, driver rod 56 may be composed of spring stainless steel or nitinol.

In this embodiment, a slot 66 is formed in needle 54 in communication with interior passage 60 to allow suture holding system 10 to exit the needle. Slot 66 terminates in a sloped wall 68 distal of needle tip 64. This sloped wall 66 helps to flip the suture holder system 10 when it is implanted in the tissue, the benefit of which will be described further below. In alternative embodiments, it is appreciated that slot 66 extend distally to the end of the needle 54, or can terminate at any point before, so long as slot 66 is large enough to accommodate suture holding system 10. Driver rod 56 is disposed distal of block 12 within the interior passage 60 and acts to advance block 12 through the passage 60 and out through slot 66.

Housing 58 is slidably received in proximal end 74 of handle 52. In one embodiment, housing 58 is provided as a depth limiter with calibration bands 70, which determine the penetration depth of needle 54 into the tissue. Locking nut 72 is tightened once the desired depth is chosen. Handle 52 includes an actuating slider 76 attached to driver rod 56 for advancing driver rod 56 towards the proximal end 62 of the needle 54. Last, reload knob 78 is provided at the distal end 80 of handle 52 and is attached to the distal end of the needle 54. Pulling back on reload knob 78 causes needle 54 to retract distally into housing 58, the function of which will be described below.

Figure 16:
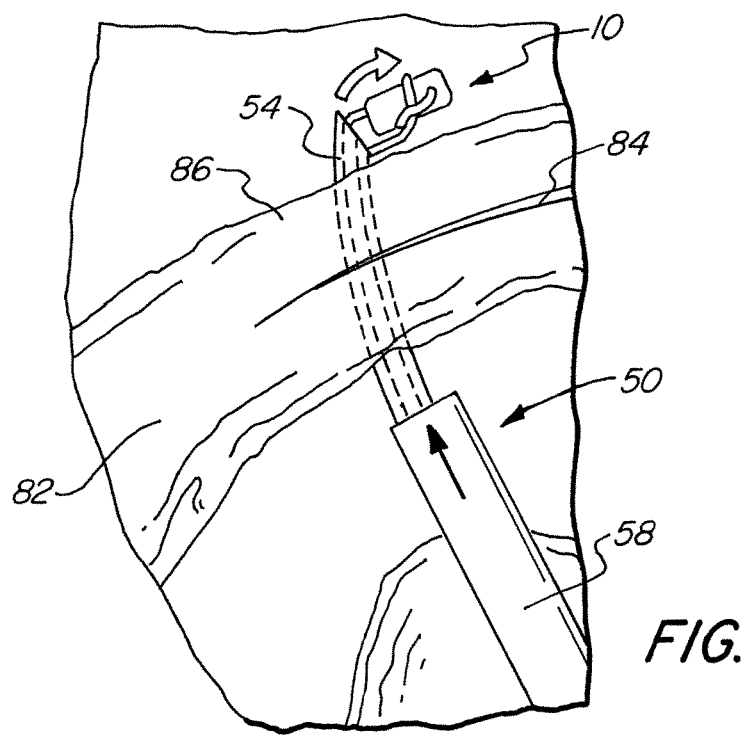
FIG. 16 is a view of an embodiment of the suture holding system and an embodiment of the delivery device of the present invention, being used to repair a tear in soft tissue.
Figure 17:
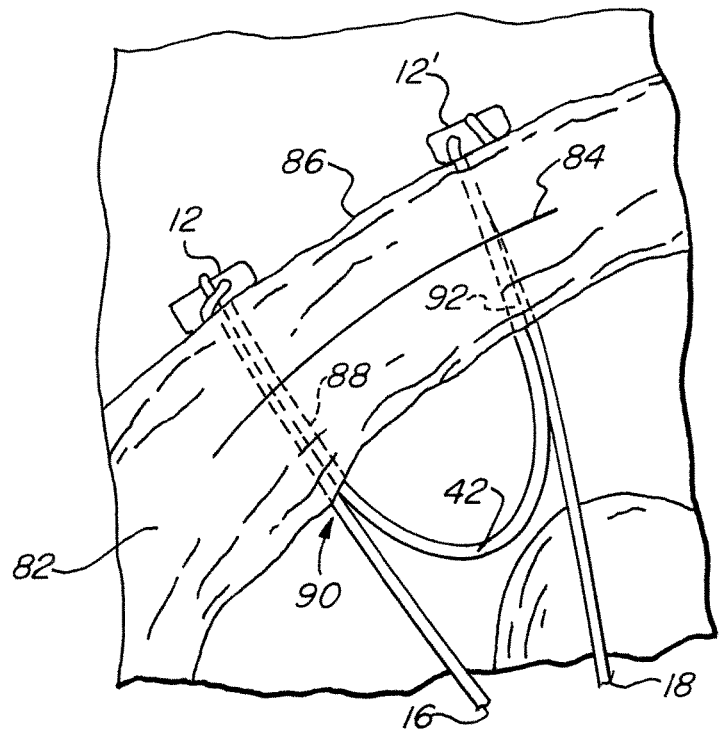
FIG. 17 is a view of an embodiment of the suture holding system having two blocks and an embodiment of the delivery device of the present invention, being used to repair a tear in soft tissue.

In use, suture 14 is attached to first block 12 and second block 12' and first block 12 is loaded into the interior passage 60 of needle 54 through slot 66. Second block 12' inserted into housing 58, such as into a recess or slot (not shown). Referring now to FIGS. 16 and 17, after suture holding system 10 is loaded into delivery device 50, a user inserts delivery device 50 into, for example, the knee joint, and passes needle 54 through soft tissue 82 and across tear 84 until needle tip 64 and first block 12 extend through tissue surface 86. The user then advances slider 76 to actuate driver rod 56 and advance first block 12 out through slot 66 of needle 54, causing first block 12 to flip. By flipping the block 12, it is ensured that the elongated bottom surface 32 of the block 12 is biased against the top surface 86 of the tissue so that the block 12 does not unintentionally pass through the puncture formed by the needle 54. Delivery device 50 and needle 54 are removed from tissue 82, leaving first block 12 remaining on the surface 86. During retraction of needle 54, a portion of suture 14 is played out of delivery device 50, with connecting portion 42 making a first pass 88 through soft tissue 82 across tear 84.

To load second block 12' into needle 54, the user pulls back on reload knob 78 to retract needle 54 and driver rod 56 into housing 58. Second block 12' is loaded into interior passage 60 through slot 66, and the user returns reload knob 78 to its original position. Needle 54 is then inserted through tissue 82, at a point spaced apart from exit point 90, across tear 84 until needle tip 64 and second block 12' extend through tissue surface 86. The user then advances slider 76 to actuate driver rod 56 and advance second block 12' out through slot 66 of needle 54, causing second block 12' to flip so that its bottom surface 32' comes to rest on tissue surface 86. Delivery device 50 and needle 54 are removed from tissue 82, leaving second block 12' remaining on the surface 86, as described above with reference to first block 12. Connecting portion 42 of suture 14 now makes a second pass 92 through soft tissue 82 across tear 84.

Proximal 16 and distal 18 ends of suture 14 now extend from tissue 82. The user grasps ends 16, 18 by hand or with forceps and pulls to shorten connecting portion 42 of suture 14 to the desired length and close tear 84. Excess suture 14 can then be trimmed off. Because suture 14 will lock against the blocks 12, 12' when any tension is placed on the connecting portion 42 of the suture 14, the free ends of the suture do not need to be knotted or tied off. This also obviates the need for a knot pusher to tighten the suture across the tear.

With the suture holding system 10 of the present invention, it is also possible to close a tear in the tissue through the use of only one block, in which case a retaining element, such as a knot, or other device would be placed on distal end 18 of suture 14 to allow the suture 14 to be tightened across the tear 84 and prevent it from loosening.

Figure 18A:
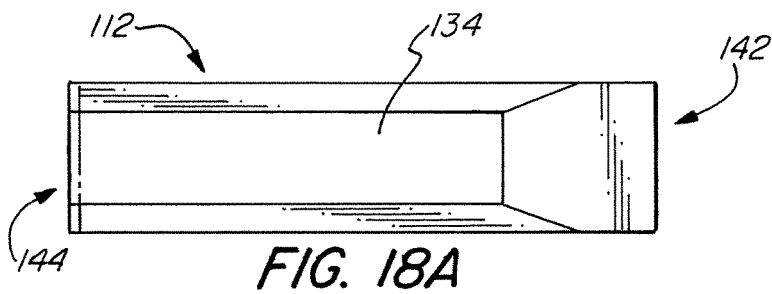
FIG. 18A is a top view of an embodiment of the block as used in the suture holding system of the present invention.
Figure 18B:
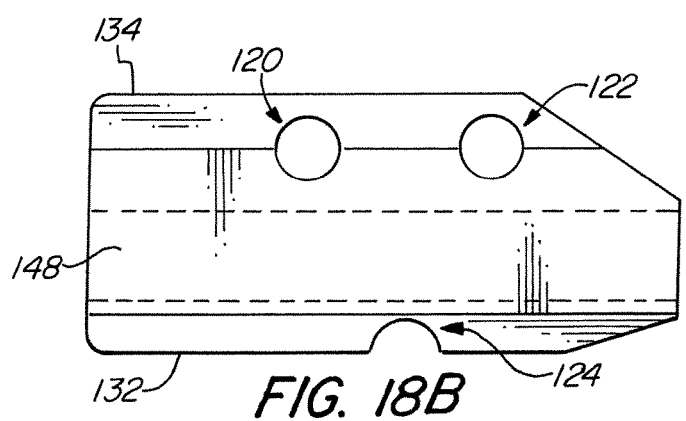
FIG. 18B is a side view of an embodiment of the block as used in the suture holding system of the present invention.
Figure 18E:
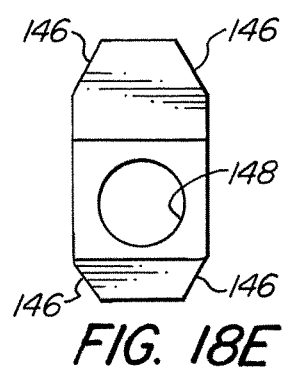
FIG. 18E is a side view of an embodiment of the block as used in the suture holding system of the present invention.
Figure 18C:
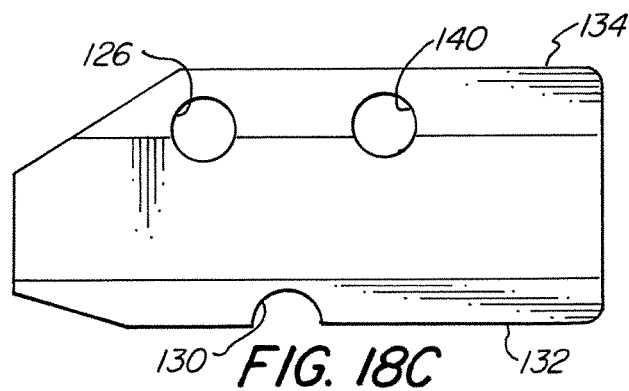
FIG. 18C is a side view of an embodiment of the block as used in the suture holding system of the present invention.
Figure 18F:
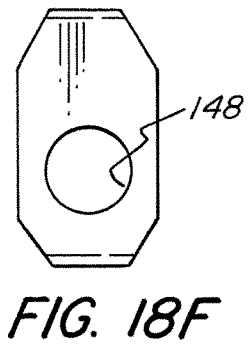
FIG. 18F is a side view of an embodiment of the block as used in the suture holding system of the present invention.
Figure 18D:
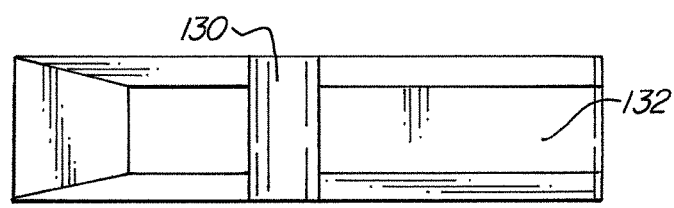
FIG. 18D is a bottom view of an embodiment of the block as used in the suture holding system of the present invention.

FIGS. 18A-18F depict an additional embodiment of the suture holding system 110 of the present invention. As shown, block 112, having bottom surface 132 and top surface 134, defines first 120, second 122 and third 124 regions for receiving a portion of suture 14. In this embodiment, first region 120 is provided as a hole 126, second region 122 is provided as a hole 140, and third region 124 is provided as a lateral notch 130 along the bottom surface 132 of the block 112. To aid in implantation of the block 112, as will be described further below, the proximal end 142 of the block 112 is tapered back towards the distal end 144 on both the top 134 and bottom 132 surfaces. Similarly, as shown in FIGS. 18E and 18F, the four corner edges 146 are beveled to give the block 114 a more rounded cross section. Block 112 is also provided with a longitudinal hole 148 for receiving a delivery needle 154.

Figure 19:
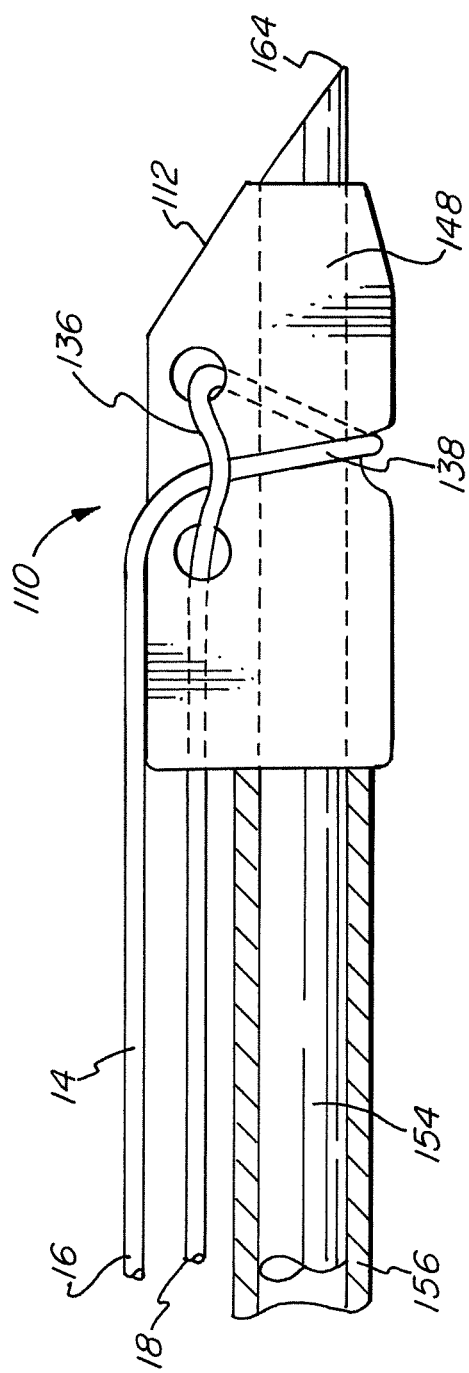
FIG. 19 is a side view of an embodiment of the suture holding system and a partial side view of an embodiment of the delivery device of the present invention.

As shown in FIG. 19, suture 14 is attached to block 112 by threading the proximal end 16 of suture 14 through hole 126 and then through hole 140, defining first suture portion 136. Proximal end 16 is then wrapped down and received in notch 130 before passing between first suture portion 136 and the block 112, defining a second suture portion 138. Again, when distal end 18 of suture 14 is pulled taught first suture portion 136 tightens, pressing second suture portion 138 against the block 112 and preventing the suture 14 from advancing in the distal direction. Block 112 may take on any of the additional block configurations described above and shown in FIGS. 5-9.

In this embodiment, needle 154, having pointed tip 164, is slidably received in hole 148 of block 112. Driver rod 156, being hollow in this embodiment, is slid over needle 154 until it abuts distal end 144 of block 112. As described above, needle 154 may also be curved at its proximal end. Driver rod 156 and needle 154 are slidably received in housing 158 of the delivery device 150. A second block 112', if desired, connected to first block 112 by suture 14, is received in recess 159 within housing 158 until it is ready to be implanted. In use, delivery system 150 operates and functions in the same manner described above and as depicted in FIGS. 16 and 17 to implant blocks 112 and 112'.

Figure 21A:
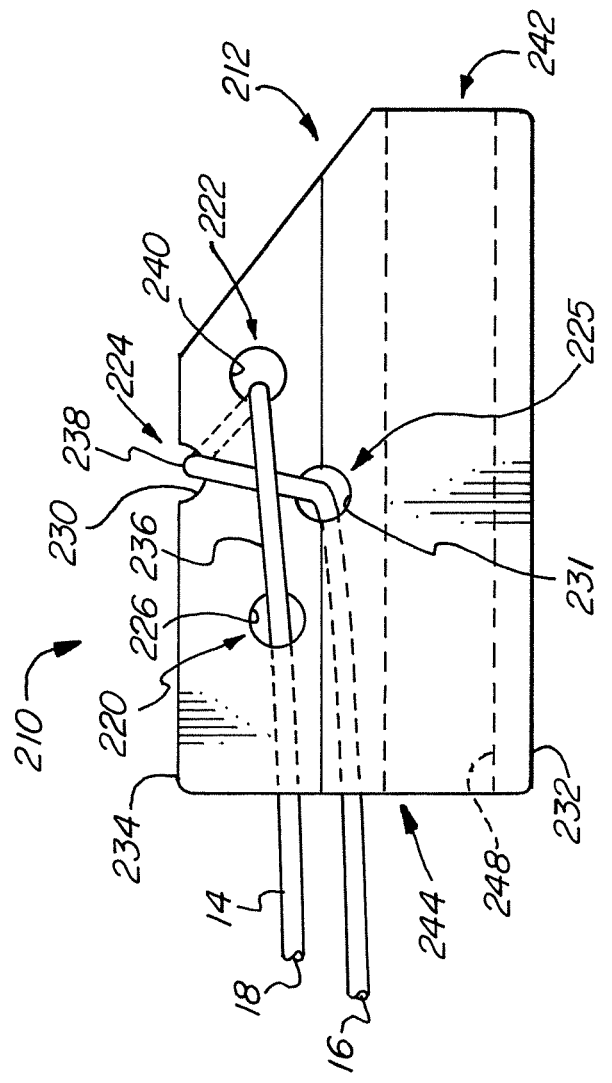
FIG. 21A is a side view of an embodiment of the suture holding system of the present invention
Figure 21B:
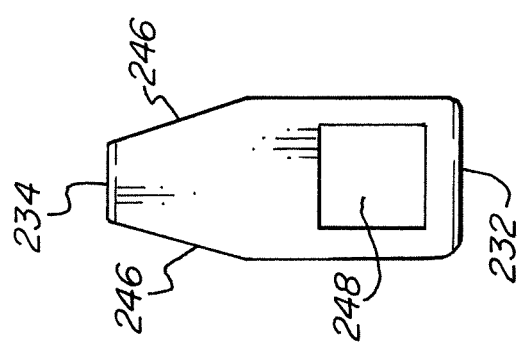
FIG. 21B is a is a front view of an embodiment of the suture holding system of the present invention

FIGS. 21A and 21B depict another embodiment of the suture holding system 210 of the present invention. As shown, block 212 having bottom surface 232 and top surface 234, defines first 220, second 222, third 224, and fourth 225 regions for receiving a portion of suture 14. In this embodiment, first region 220 is provided as a hole 226, second region 222 is provided as a hole 240, third region 224 is provided as a lateral notch 230 along the top surface 234 of the block 212, and fourth region 225 is provided as a hole 231. To aid in implantation of the block 212 the proximal end 242 is tapered back towards the distal end 244 on the top surface 234. Similarly, as shown in FIG. 21B, the top corner edges 246 are beveled.

Block 212 is also provided with a square-shaped longitudinal hole 248 for receiving a delivery needle. In this embodiment, the delivery needle would also be square. By providing the delivery needle and the longitudinal hole 248 with a square shape, the block 212 will be prevented from rotating about the delivery needle during insertion of the suture holding system 210 into the tissue. It is appreciated that any non-circular longitudinal hole and delivery needle could be used to accomplish this goal.

As shown in FIG. 21A, suture 14 is attached to block 212 by threading the proximal end 16 of suture 14 through hole 226 and then through hole 240, defining first suture portion 236. Proximal end 16 is then wrapped around the back of the block 212 and received in notch 230 before passing between first suture portion 236 and the block 212, defining a second suture portion 238. Proximal end 16 is then passed through hole 231. Again, when distal end 18 of suture 14 is pulled taught first suture portion 236 tightens, pressing second suture portion 238 against the block 212 and preventing the suture 14 from advancing in the distal direction. Block 212 may take on any of the additional block configurations described above and shown in FIGS. 5-9.

Figure 20:
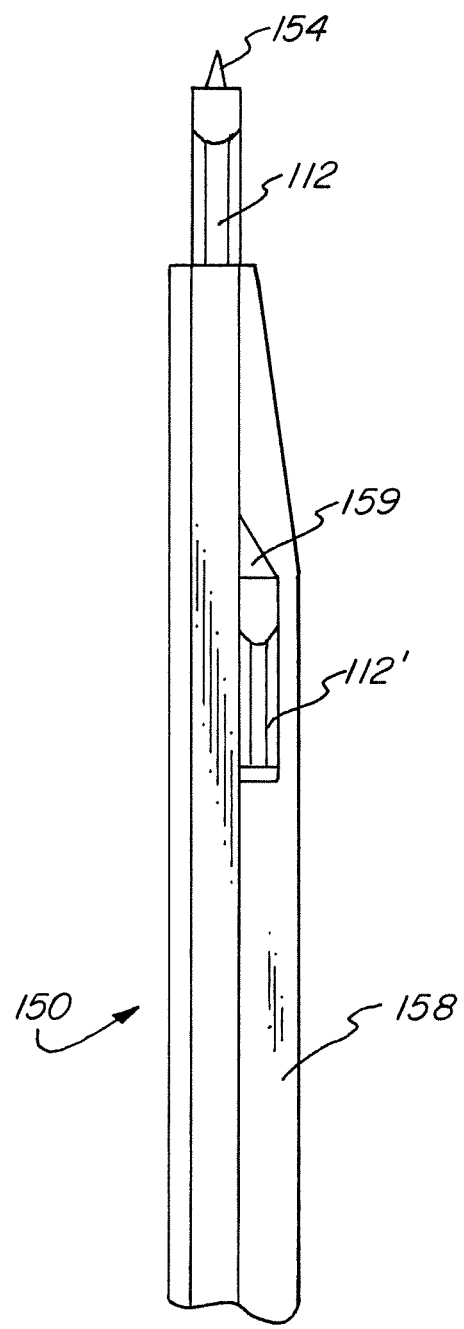
FIG. 20 is a side view of an embodiment of the suture holding system and a partial side view of an embodiment of the delivery device of the present invention.

Block 212 is implanted into tissue in the same manner as described above with respect to the embodiment shown in FIGS. 18-20 and may also be used with a second block.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A suture holding system comprising:
   a block having:
      a front surface;
      a back surface;
      a hole extending from said front surface to said back surface;
      a first notch extending laterally from said front surface all the way to said back surface along at least a portion of a top surface of the block; and
      a second notch on a bottom surface of the block;
   and
   a suture having a first suture portion and a second suture portion, wherein the first suture portion extends from a first end to the second suture portion, wherein the second suture portion extends from the first suture portion to a second end, wherein starting from said first end, said first suture portion passes only once through said hole in a single direction from said back surface to said front surface and thereafter is received in said second notch from said front surface to said back surface, said second suture portion being held against said block by a section of said first suture portion that extends between said hole and said second notch;
   wherein said second suture portion following said first suture portion wraps around said back surface of said block towards said top surface and is then at least partially received in said first notch from said back surface to said front surface before passing between said first suture portion and said front surface of said block.

2. The suture holding system of claim 1 further comprising a second block, a portion of said suture being received in said second block.

3. The suture holding system of claim 1 wherein said block is substantially rectangular in shape.

4. The suture holding system of claim 1 wherein said block has a tapered edge.

5. The suture holding system of claim 1 wherein said block has a length, height, and depth.

6. The suture holding system of claim 5 wherein said block length is about 2.5 times longer than said block height.

7. The suture holding system of claim 5 wherein said block length is about 3 times longer than said block height.

8. The suture holding system of claim 5 wherein said block height is about 1.5 times longer than said block depth.

9. The suture holding system of claim 5 wherein said block height is about 2 times longer than said block depth.

10. A suture holding system comprising:
    a block having:
       a front surface;
       a back surface;
       a bottom surface;
       a top surface;
       a first hole extending from said front surface to said back surface; and
       a first notch extending laterally from said front surface all the way to said back surface along at least a portion of the top surface of the block; and
    a suture having a first suture portion and a second suture portion, wherein the first suture portion extends from a first end to the second suture portion, wherein the second suture portion extends from the first suture portion to a second end, wherein the first suture portion extends from a first end to the second suture portion, wherein the second suture portion extends from the first suture portion to a second end, wherein starting from said first end, said first suture portion passes only once through said first hole in a single direction from said back surface to said front surface and thereafter passes under the bottom surface of the block from said front surface to said back surface, wherein said second suture portion following said first suture portion passes from said bottom surface over said back surface to said top surface and is then received in said first notch from said back surface to said front surface before being held against said front surface of said block by a section of said first suture portion that extends between said hole and said bottom surface of the block.

11. The suture holding system of claim 10 wherein said block further comprises a second notch on the bottom surface of the block, said first suture portion being received in said first hole and said second notch.

12. The suture holding system of claim 10 wherein said block further comprises a second hole extending therethrough, said first suture portion being received in said first hole and said second hole.

13. A suture holding system comprising:
a first block comprising:
  a first region for receiving a portion of a suture;
  a second region for receiving a portion of a suture;
  a third region for receiving a portion of a suture;
  a suture having a first suture portion and a second suture portion, wherein the first suture portion extends from a first end to the second suture portion, wherein the second suture portion extends from the first suture portion to a second end, said first suture portion being received in said first region and said second region, said second suture portion being at least partially received in said third region before being held against said first block by said first suture portion; and
a second block, receiving a portion of the suture, comprising:
  a fourth region for receiving a portion of a suture;
  a fifth region for receiving a portion of a suture; and
  a sixth region for receiving a portion of a suture;
  said second block being rotated 180 degrees with respect to said first block;
said suture further having a third suture portion and a fourth suture portion, said third suture portion being at least partially received in said fourth region and said fifth region, said fourth suture portion being at least partially received in said sixth region before being held against said second block by said third suture portion,
wherein said first region comprises a hole extending from a front surface of said first block to a back surface of said first block and, starting from the first end of said suture, said first suture portion passes only once through said hole in a single direction from said back surface to said front surface and thereafter is received in said second region from said front surface to said back surface, and wherein said second suture portion following said first suture portion wraps around said back surface and is then at least partially received in said third region before being held against said front surface of said first block by a section of said first suture portion that extends between said hole and said second region of said first block.

14. The suture holding system of claim 13 wherein said second region comprises a hole extending through at least a portion of the first block.

15. The suture holding system of claim 13 wherein said second region comprises a notch extending from said front surface all the way to said back surface along at least a portion of the first block.

16. The suture holding system of claim 13 wherein said third region comprises a notch extending along at least a portion of the first block.

17. The suture holding system of claim 13 wherein said fourth region comprises a hole extending through at least a portion of the second block.

18. The suture holding system of claim 13 wherein said fifth region comprises a hole extending through at least a portion of the second block.

19. The suture holding system of claim 13 wherein said fifth region comprises a notch extending along at least a portion of the second block.

20. The suture holding system of claim 13 wherein said sixth region comprises a notch extending along at least a portion of the second block.

* * * * *